United States Patent [19]

Bollag et al.

[11] 4,200,647

[45] Apr. 29, 1980

[54] VITAMIN A COMPOSITIONS TO TREAT RHEUMATIC DISEASE

[75] Inventors: Werner Bollag, Basel; Kurt Reber, Ettingen, both of Switzerland

[73] Assignee: Hoffmann-La Roche Inc., Nutley, N.J.

[21] Appl. No.: 968,712

[22] Filed: Dec. 12, 1978

[30] Foreign Application Priority Data

Dec. 21, 1977 [CH] Switzerland .................. 15795/77

[51] Int. Cl.$^2$ ............... A61K 31/07; A61K 31/20; A61K 31/38; A61K 31/215
[52] U.S. Cl. .......................... 424/305; 424/275; 424/318; 424/344
[58] Field of Search ............ 424/344, 305, 318, 275

[56] References Cited

U.S. PATENT DOCUMENTS

| 3,729,568 | 4/1973 | Kligman | 424/318 |
| 4,054,589 | 10/1977 | Bollag et al. | 260/408 |
| 4,105,681 | 8/1978 | Bollag et al. | 260/404 |

FOREIGN PATENT DOCUMENTS

752928 7/1970 Belgium.

OTHER PUBLICATIONS

Chem. Abst., 89-108758e, (1978).
Chem. Abst., 76-158354, (1972).
Prutkin, Journal of Investigative Dermatology, vol. 49, No. 2, pp. 165-172.

*Primary Examiner*—Stanley J. Friedman
*Attorney, Agent, or Firm*—Jon S. Saxe; Bernard S. Leon; George W. Johnston

[57] ABSTRACT

Compositions and methods for treating rheumatic diseases with vitamin A compounds are disclosed.

8 Claims, No Drawings

VITAMIN A COMPOSITIONS TO TREAT RHEUMATIC DISEASE

BACKGROUND OF THE INVENTION

1. Field of the Invention

This invention relates to the use of vitamin A compounds in the treatment of rheumatic diseases.

2. Description of the Prior Art

In the past, vitamin A compounds also known as retinoids were subjected to extensive clinical testing and were found to be effective in the treatment of various disorders in mammals and particularly in humans. For example, a large number of dermatologists have experimentally treated certain skin diseases such as neoplasias, acne, psoriasis and other dermatological conditions by the topical administration of vitamin A compounds. Their work has produced great advances in the treatment of such disorders. Retinoids also have been clinically utilized to treat tumors and therapeutical progress has been made with retinoids in these areas.

Surprisingly, we have now found that other pathological conditions can be successfully treated by the oral administration of retinoids.

SUMMARY OF THE INVENTION

We have discovered that retinoids are useful in treating rheumatic diseases. In accordance with our discovery, patients suffering from rheumatic disease are orally administered a composition comprising an effective amount of a retinoid and a medicinally inert pharmaceutically acceptable carrier material. The pharmaceutical compositions of this invention are significantly effective in treating rheumatoid arthritis, Bechterew's ankylopoietic spondylarthritis and psoriatic arthropathy. Compositions having 9-(4-methoxy-2,3,6-trimethylphenyl)-3,7-dimethyl-nona-2,4,6,8-tetraen-1-oic acid ethyl ester as their active ingredient are preferred.

DETAILED DESCRIPTION OF THE INVENTION

This invention concerns the use of retinoids in the treatment of rheumatic diseases.

In accordance with this invention, a pharmaceutical composition comprising an amount of a retinoid which is effective in the treatment of a rheumatic disease and a medicinally inert pharmaceutically acceptable carrier material is orally administered to a mammal such as a human suffering from a rheumatic disease.

Rheumatic diseases include diseases of the muscles, tendons, joints, bones or sinews, which are generally characterized by inflammation and/or degeneration. Rheumatic diseases often are accompanied by intense pain, stiffness, loss of muscular strength and deformation. Examples of rheumatic diseases are rhuematoid arthritis (inflammation of several joints), Bechterew's ankylopoietic spondylarthritis (a chronic progressive arthritis of the vertebrae) and psoriatic arthropathy (inflammation and/or degeneration of the joints associated with psoriasis of the skin.

As used herein, "retinoids" denote vitamin A in its naturally occurring forms such as retinol, retinal, retinyl esters, retinoic acid as well as synthetic analogs of vitamin A. The ring on the analogs may be aromatic or heteroaromatic and the side chain may be optionally substituted with a halide such as chloride. The terminal group may be oxidized, reduced, esterified, etc. The alkali metal (sodium, potassium, etc.) and alkaline earth metal (magnesium, calcium, etc.) salts of a retinoid carboxylic acid are also included herein.

Examples of retinoids included within the present invention are vitamin A acid, 13-cis-vitamin A acid, 9-(4-methoxy-2,3,6-trimethylphenyl)-3,7-dimethyl-nona-2,4,6,8-tetraen-1-oic acid ethylamide, 9-(2,6-dichloro-4-methoxy-5-methyl-phenyl)-3,7-dimethyl-nona-2,4,6,8-tetraen-1-oic acid ethyl ester, 4-O-α-D-glucopyranosyl-D-glucopyranosyl-9-(4-methoxy-2,3,6-trimethyl-phenyl)-3,7-dimethyl-nona-2,4,6,8-tetraenate, 3,7-dimethyl-9-(2,4,5-trimethyl-3-thienyl)-nona-2,4,6,8-tetraen-1-oic acid ethyl ester, 9-(4-methoxy-2,4,6-trimethyl-phenyl)-4-fluoro-3,7-dimethyl-nona-2,4,6,8-tetraen-1-oic acid ethyl ester and especially 9-(4-methoxy-2,3,6-trimethylphenyl)-3,7-dimethyl-nona-2,4,6,8-tetraen-1-oic acid ethyl ester.

These compounds and methods for their preparation are known. See e.g., U.S. Pat. No. 3,746,730, U.S. Pat. No. 3,931,257, U.S. Pat. No. 3,950,418, U.S. Pat. No. 4,054,589 and U.S. Pat. No. 4,061,656.

Pharmaceutical compositions which have as their active ingredient 9-(4-methoxy-2,3,6-trimethylphenyl)-3,7-dimethyl-nona-2,4,6,8-tetraen-1-oic acid ethyl ester are preferred.

The pharmaceutical preparations of the present invention can be prepared by coventional techniques and procedures. Illustratively, the compositions can be prepared by adding the retinoid as the active ingredient to pharmaceutically acceptable, non-toxic, inert, solid or liquid carriers which are usually included in such preparations. The pharmaceutical preparations are administered orally using conventional techniques. Suitable preparations for oral administration are, for example, tablets, capsules, dragees, syrups, suspension and solutions.

In addition to the active retinoids of this invention, the pharmaceutical preparations can contain any conventional pharmaceutically acceptable inert or pharmacodynamically active additives. For example, tablets or granules can contain a series of pharmaceutically acceptable binders, fillers, carrier materials or diluents. Liquid preparations can, for example, take the form of sterile water-miscible solutions. Capsules can contain a pharmaceutically acceptable filler or thickener. Furthermore, pharmaceutically acceptable flavor-improving additives and pharmaceutically acceptable substances commonly used as preservatives, stablizers, moisture retainers or emulsifiers, salts for varying the osmotic pressure, buffers and other pharamceutically acceptable additives can also be present in the pharmaceutical preparations.

The aforementioned pharmaceutically acceptable carrier materials and diluents are well known to the pharmaceutical compound art and can be organic or inorganic substances such as water, gelatin, lactose, magnesium stearate, talc, gum arabic, polyalkyleneglycols and the like. It is, of course, a prerequisite that all adjuvants used in the preparation of the pharmaceutical preparations be non-toxic and pharmaceutically acceptable.

Conventional pharmaceutically acceptable antioxidants (e.g., tocopherol, N-methyl-α-tocopheramine butylated hydroxyanisole and butylated hydroxytoluene) can also be incorporated into the pharmaceutical preparations of this invention.

The dosages in which the compounds are administered can be varied according to the mode and route of administration and according to the requirements of the patient. For example, the dosage can be varied and lowered, if necessary, to avoid potential side effects such as loss or hair or cheilitis. Advantageously, the pharmaceutical compositions of the present invention are administered at a daily dose of about 0.25 to about 2 mg. of retinoid per kg. of body weight and preferably at about 0.5 to about 1 mg. of retinoid per kg. body weight. The compositions can be administered to the patient as a single dose or divided over several part doses.

The duration of the treatment utilizing the pharmaceutical compositions of the present invention depends upon the individual circumstances of the patient and can vary from a few weeks to several months.

To examine their pharmacodynamic activity in humans, pharmaceutical compositions of the present invention were administered to various patients suffering from rheumatic diseases. The results utilizing 9-(4-methoxy-2,3,6-trimethylphenyl)-3,7-dimethyl-nona-2,4,6,8-tetraen-1-oic acid ethyl ester for treating psoriatic arthropathy and rheumatoid arthritis are presented in Tables I–IV. The tabulation serves as a guideline for the use of the pharmaceutical compositions of the present invention having as their active ingredient the above compound or other retinoids.

In the Tables, the results of the treatment are assessed as follows:

− = no improvement
+ = moderate improvement
++ = good improvement

The articular index noted in the Tables was determined by the method of Ritchie et al., Quart. J. Med. New Series XXXVII, No. 147 (1968), page 393 et seq. In the Tables, ♂ means male human and ♀ means female human.

Table I

| Patient Sex/age | Articular index | Morning stiffness | Functional status | Pain |
|---|---|---|---|---|
| ♂ 35 | + |  | + | + |
| ♂ 28 | ++ |  | − | ++ |
| ♂ 20 | ++ |  |  |  |
| ♂ 39 | ++ | ++ | − | + |
| ♀ 43 | ++ | ++ | − | + |
| ♀ 32 | ++ | ++ | − | ++ |

Treatment of psoriatic arthropathy
Dosage: 1 mg/kg/day; duration of treatment: 4 weeks Table II Treatment of psoriatic arthropathy

| Patient Sex/age | Dosage [mg/day] | Articular index | Morning stiffness | Functional status | Pain |
|---|---|---|---|---|---|
| ♂ 20 | 35 (1 month) |  |  |  |  |
|  | 25 (2 months) | ++ |  |  | ++ |
| ♀ 51 | 60 (6 weeks) | ++ | ++ | − | + |
|  | 35 (1 week) |  |  |  |  |
| ♀ 43 | 25 (6 weeks) |  |  |  |  |
|  | 50 | + |  | + | + |
| ♂ 29 | 95 (4 weeks) | ++ | ++ | − | ++ |
|  | 100 (3 weeks) |  |  |  |  |
|  | 50 (7.5 weeks) |  |  |  |  |
| ♂ 39 | 75 (8 weeks) | ++ |  | − | ++ |
| ♀ 16 | 30 (9 weeks) | ++ |  | − | − |
|  | 20 (3 weeks) |  |  |  |  |
| ♀ 32 | 30 (6 weeks) | ++ |  | + | ++ |
| ♀ 64 | 50 (13 weeks) | ++ | ++ | ++ | ++ |
| ♀ 56 | 70 (12 weeks) | + | ++ | + | + |
|  | 50 (6 weeks) |  |  |  |  |

Table III

Treatment of rheumatoid arthritis
Dosage: 1 mg/kg/day; duration of treatment: 4 weeks

| Patient Sex/age | Articular index | Morning stiffness | Functional status | Pain |
|---|---|---|---|---|
| ♀ 64 | + | − | − | − |
| ♀ 52 | ++ | ++ | − | + |
| ♀ 40 | + | ++ | − | + |
| ♀ 75 | ++ | ++ | − | + |

Table IV

Treatment of rheumatoid arthritis

| Patient Sex/age | Dosage [mg/day] | Articular index | Strength of grip | Morning stiffness | Functional status | Pain |
|---|---|---|---|---|---|---|
| ♀ 54 | 50 (14 weeks) | ++ | + | ++ | + | ++ |
| ♀ 57 | 60 (4 weeks) | + | + | + | + | + |
|  | 50 (7 weeks) |  |  |  |  |  |
|  | 40 (3 weeks) |  |  |  |  |  |
|  | 50 (2 weeks) |  |  |  |  |  |
| ♀ | 50 (18 weeks) | + |  |  | + | + |

To examine their pharmacodynamic activity in mammals other than man, the retinoids of the present invention were administered to rats using the adjuvant arthritis model as described in Heffter-Heubner: Handbook of Experimental Pharmacology, Vol. XVI/8, O. Eichler (editor): Erzeugung von Krankheitszuständen durch das Experiment. Teil 8, Stütz- und Hartgewebe, pg 189 ff, Springer, Heidelberg und New York, 1969. The results are tabulated in Tables V–VII. For Tables V and VII, the antiarthritic activity of the retinoids were determined as follows:

Method: Test and control groups of 6 to 8 rats were given an intractuaneous injection of 0.1 ml. of complete Freund adjuvant. Immediately before the injection of the adjuvant and 3 weeks afterwards, the diameter of all 4 paws of each rat were determined. The relevant measured value for each animal was defined as the sum of the 4 paw diameters. Test animals were treated with a retinoid for 2 weeks, starting 3 days before injection of the adjuvant. Control animals were not administered the retinoid.

Evaluation: The mean percentage change of the paw diameters of the test animals ($\Delta T\%$) and that of the control animals ($\Delta C\%$) were calculated. The relative action was defined and calculated in accordance with the following equation:

$$100\% - (\Delta T\%/\Delta C\% \cdot 100)\%$$

A large relative action indicated significant activity of the retinoid tested.

The test results utilizing 9-(4-methoxy-2,3,6-trimethylphenyl)-3,7-dimethyl-nona-2,4,6,8-tetraen-1-oic acid ethyl ester as the retinoid are tabulated in Table V.

Table VI illustrates the action of 9-(4-methoxy-2,3,6-trimethylphenyl)-3,7-dimethylnona-2,4,6,8-tetraene-1-acid ethyl ester (A), of its corresponding ethylamide (B) and of vitamin A-acid (C) utilizing the previously described test method.

In a further series of tests, a procedure analogous to that described above was followed, but the treatment of the test animals with the retinoid started 3 weeks after injection of the adjuvant and was then continued for 4 additional weeks (total 7 weeks for the experiment). The diameter of all four paws of each control and test rat were measured at the end of the second week of the experiment (immediately before the injection of the adjuvant) and after the fourth (first week of treatment), fifth (second week of treatment), sixth (third week of treatment) and seventh (fourth week of treatment) week of the experiment.

The percentage of regression of paw oedema was defined as follows:

$$100\% - \left(\frac{\text{paw diameter after indicated week of treatment}}{\text{paw diameter immediately before any treatment}}\right)\%$$

The percentage of regression of paw oedema was calculated after each of the four weeks of treatment. A large percentage of regression indicated significant activity of the retinoid. The test results utilizing 9-(4-methoxy-2,3,6-trimethylphenyl)-3,7-dimethyl-nona-2,4,6,8-tetraen-1-oic acid ethyl ester as the retinoid are tabulated in Table VII.

Table V

| Dose [mg/kg] | Number of animals | Paw diameter Beginning of test | End of test | Difference | Relative action % |
| --- | --- | --- | --- | --- | --- |
| 0* | 8 | 24.9 | 44.0 | 19.1 | 0 |
| 15 | 8 | 25.0 | 37.5 | 12.5 | 34.8 |
| 30 | 8 | 25.2 | 34.0 | 8.8 | 54.3 |
| 60 | 4 | 25.9 | 29.2 | 3.3 | 83.2 |

*control

Table VI

| Compound | Dose [mg/kg] | Number of animals | Paw diameter Beginning of test | End of test | Difference | Relative action % |
| --- | --- | --- | --- | --- | --- | --- |
| Control | 0 | 8 | 24.8 | 44.1 | 19.3 | 0 |
| A | 30 | 8 | 24.8 | 33.0 | 8.2 | 57.4 |
| B | 30 | 8 | 24.5 | 34.0 | 9.5 | 50.0 |
| C | 30 | 8 | 24.6 | 34.2 | 9.6 | 49.9 |

Table VII

| Dose [mg/kg] | Percentage regression of the paw oedema 1 week* | 2 weeks* | 3 weeks* | 4 weeks* | Duration of treatment |
| --- | --- | --- | --- | --- | --- |
| 0+ | −3x | 3 | 7.1 | 7.6 | |
| 60 | 12 | 21 | 25 | 28 | | x i.e. increase in oedema
+control
*after the indicated weeks of treatment

The following Examples illustrate the present invention. Unless otherwise stated, temperatures are in degrees Celsius (°C.) and the "active ingredient" is 9-(4-methoxy-2,3,6-trimethylphenyl)-3,7-dimethyl-nona-2,4,6,8-tetraen-1-oic acid ethyl ester.

EXAMPLE 1

| Capsule for oral administration | | |
| --- | --- | --- |
| Active ingredient | 25 | mg. |
| Lactose | 52 | mg. |
| Corn starch | 20 | mg. |
| Microcrystalline cellulose | 40 | mg. |
| Talc | 2.5 | mg. |
| Magnesium stearate | 0.5 | mg. |

The active ingredient was mixed with the adjuvant in a suitable mixer, milled in a suitable miller and filled, manually or mechanically, into gelatin push-fit capsules of size No. 4.

EXAMPLE 2

| Capsule for oral administration | | |
| --- | --- | --- |
| Active ingredient | 10 | mg. |
| Lactose | 82 | mg. |
| Corn starch | 45 | mg. |
| Talc | 2.5 | mg. |
| Magnesium stearate | 0.5 | mg. |

The active ingredient was mixed with the adjuvants in a suitable mixer, milled and filled, manually or mechanically, into gelatin push-fit capsules of size No. 4.

EXAMPLE 3

| Capsule for oral administration | | |
| --- | --- | --- |
| Active ingredient | 5 | mg. |
| Lactose | 102 | mg. |
| Microcrystalline cellulose | 30 | mg. |
| Talc | 2.5 | mg. |
| Magnesium stearate | 0.5 | mg. |

The active ingredient was mixed with the adjuvants in a suitable mixer, milled in a suitable miller and filled, manually or mechanically, into gelatin push-fit capsules of size No. 4.

EXAMPLE 4

| Tablets for oral administration | | |
| --- | --- | --- |
| Active ingredient | 25 | mg. |
| Lactose | 20 | mg. |
| Corn starch | 30 | mg. |
| Microcrystalline cellulose | 42 | mg. |
| Talc | 2.5 | mg. |
| Magnesium stearate | 0.5 | mg. |

The active ingredient was mixed with lactose and granulated using a corn starch paste. The remainder of the above adjuvants was then admixed therein and the mass was tableted. The tablets were then coated with a water-soluble or water-swellable lacquer.

EXAMPLE 5

| Tablets for oral administration | | |
| --- | --- | --- |
| Active ingredient | 10 | mg. |
| Lactose | 30 | mg. |
| Corn starch | 30 | mg. |
| Microcrystalline cellulose | 47 | mg. |
| Talc | 2.5 | mg. |
| Magnesium stearate | 0.5 | mg. |

The active ingredient was mixed with lactose and granulated using a corn starch paste. The remainder of the adjuvants were then admixed therein and the mass was tableted. The tablets were then coated with a water-soluble or water swellable lacquer.

EXAMPLE 6

| Tablets for oral administration | | |
| --- | --- | --- |
| Active ingredient | 5 | mg. |
| Lactose | 45 | mg. |
| Corn starch | 30 | mg. |
| Microcrystalline cellulose | 37 | mg. |
| Talc | 2.5 | mg. |
| Magnesium stearate | 0.5 | mg. |

The active ingredient was mixed with lactose and granulated using a corn starch paste. The remainder of the adjuvants was then admixed therein and the mass was tableted. The tablets were then coated with a water-soluble or water-swellable lacquer.

We claim:

1. A method for orally treating rheumatic disease in a mammal comprising orally administering to said mammal a retinoid or a pharmaceutically acceptable salt thereof, in an amount effective for treating rheumatic disease.

2. The method of claim 1 wherein the retinoid is vitamin A in its naturally occurring form or a synthetic analog of vitamin A.

3. The method of claim 1 wherein the retinoid is selected from the group consisting of vitamin A acid, 13-cis-vitamin A acid, 9-(4-methoxy-2,3,6-trimethyl-phenyl)-3,7-dimethyl-nona-2,4,6,8-tetraen-1-oic acid ethylamide, 9-(2,6-dichloro-4-methoxy-5-methyl-phenyl)-3,7-dimethyl-nona-2,4,6,8-tetraen-1-oic acid ethyl ester, 4-O-α-D-glucopyranosyl-D-glucopyranosyl-9-(4-methoxy-2,3,6-trimethyl-phenyl)-3,7-dimethyl-nona-2,4,6,8-tetraenate, 3,7-dimethyl-9-(2,4,5-trimethyl-3-thienyl)-nona-2,4,6,8-tetraen-1-oic acid ethyl ester, 9-(4-methoxy-2,3,6-trimethyl-phenyl)4-fluoro-3,7-dimethyl-nona-2,4,6,8-tetraen-1-oic acid ethyl ester and 9-(4-methoxy-2,3,6-trimethylphenyl)-3,7-dimethyl-nona-2,4,6,8-tetraen-1-oic acid ethyl ester, or the pharmaceutically acceptable salts thereof.

4. The method of claim 1 or 2 wherein the rheumatic disease is rheumatoid arthritis.

5. The method of claim 1 or 2 wherein the rheumatic disease is Bechterew's ankylopoietic spondylarthritis.

6. The method of claim 1 or 2 wherein the rheumatic disease is psoriatic arthopathy.

7. The method of claim 3 wherein the composition is orally administered at a daily dose of about 0.25 to about 2.0 mg/kg. of body weight of said mammal.

8. The method of claim 3 or 7 wherein the retinoid is 9-(4-methoxy-2,3,6-trimethylphenyl)-3,7-dimethyl-nona-2,4,6,8-tetraen-1-oic acid ethyl ester.

* * * * *